United States Patent [19]
Poli et al.

[11] Patent Number: 5,192,269
[45] Date of Patent: Mar. 9, 1993

[54] MULTI-VALVE MANIFOLD FOR DRUG INFUSION SYSTEMS

[75] Inventors: Robert G. Poli, Campbell; Noel L. Johnson, San Jose, both of Calif.

[73] Assignee: Abbott Laboratories, Abbott Park, Ill.

[21] Appl. No.: 734,828

[22] Filed: Jul. 24, 1991

[51] Int. Cl.⁵ .............................. A61M 37/00
[52] U.S. Cl. ........................... 604/82; 604/90; 604/246; 137/606; 137/896
[58] Field of Search ................... 604/65–67, 604/49, 80–82, 89–91, 173, 246, 247, 83, 30; 222/132, 135, 136, 145, 330; 137/602, 606, 896–897

[56] References Cited

U.S. PATENT DOCUMENTS

| | | |
|---|---|---|
| 1,634,949 | 7/1927 | Le Valley . |
| 1,867,478 | 7/1932 | Stelzner . |
| 2,913,000 | 11/1959 | Roberts ................... 137/525 |
| 3,416,567 | 12/1968 | Von Dardel et al. ........... 137/604 |
| 3,566,930 | 3/1971 | Kirschner ................... 604/80 X |
| 3,626,978 | 12/1971 | Hoekstra ................... 137/525.3 |
| 3,799,427 | 3/1974 | Goglio ..................... 383/103 |
| 3,865,133 | 2/1975 | Alford ..................... 137/512 |
| 3,954,121 | 5/1976 | Kardos ..................... 137/525 |
| 3,990,439 | 11/1976 | Klinger .................... 128/142.4 |
| 4,168,724 | 9/1979 | Graffunder et al. ........... 137/606 |
| 4,217,921 | 8/1980 | Gidner ..................... 137/218 |
| 4,246,932 | 1/1981 | Raines ..................... 137/512 |
| 4,437,490 | 3/1984 | Demers et al. .............. 137/512.4 |
| 4,535,820 | 8/1985 | Raines ..................... 137/854 |
| 4,558,845 | 12/1985 | Hunkapiller ................ 251/331 |
| 4,565,214 | 1/1986 | Parman ..................... 137/512.15 |
| 4,585,623 | 4/1986 | Chandler ................... 422/57 |
| 4,597,412 | 7/1986 | Stark ...................... 137/606 |
| 4,632,151 | 12/1986 | Glover ..................... 137/854 |
| 4,666,429 | 5/1987 | Stone ...................... 604/83 |
| 4,696,671 | 9/1987 | Epstein et al. ............. 604/67 |
| 4,703,913 | 11/1987 | Hunkapiller ................ 251/61.1 |
| 4,712,574 | 12/1987 | Perrott .................... 137/217 |
| 4,729,401 | 3/1988 | Raines ..................... 137/512 |
| 4,871,353 | 10/1989 | Thomsen .................... 604/83 |
| 4,871,353 | 10/1989 | Thomsen .................... 604/83 |
| 4,908,018 | 3/1990 | Thomsen .................... 604/83 |
| 4,915,688 | 4/1990 | Bischof et al. ............. 604/83 |
| 4,925,444 | 5/1990 | Orkin et al. ............... 604/80 |
| 5,020,562 | 6/1991 | Richmon et al. ............. 137/15 |
| 5,037,390 | 8/1991 | Raines et al. .............. 604/83 |

*Primary Examiner*—C. Fred Rosenbaum
*Assistant Examiner*—C. Maglione
*Attorney, Agent, or Firm*—Harry G. Thibault; Robert E. Wexler

[57] ABSTRACT

A multiple inlet manifold for mixing and transporting therethrough fluids under pressure comprising a manifold body including a plurality of valve inlets and a single outlet, a mixing chamber provided between the valve inlets and the outlet, and a flexible membrane disposed between the valve inlets and the outlet to retain the valve inlets normally closed at selected levels of fluid pressure. Fluid flow under pressure opens a valve inlet to enable fluid flow into the mixing chamber.

15 Claims, 4 Drawing Sheets

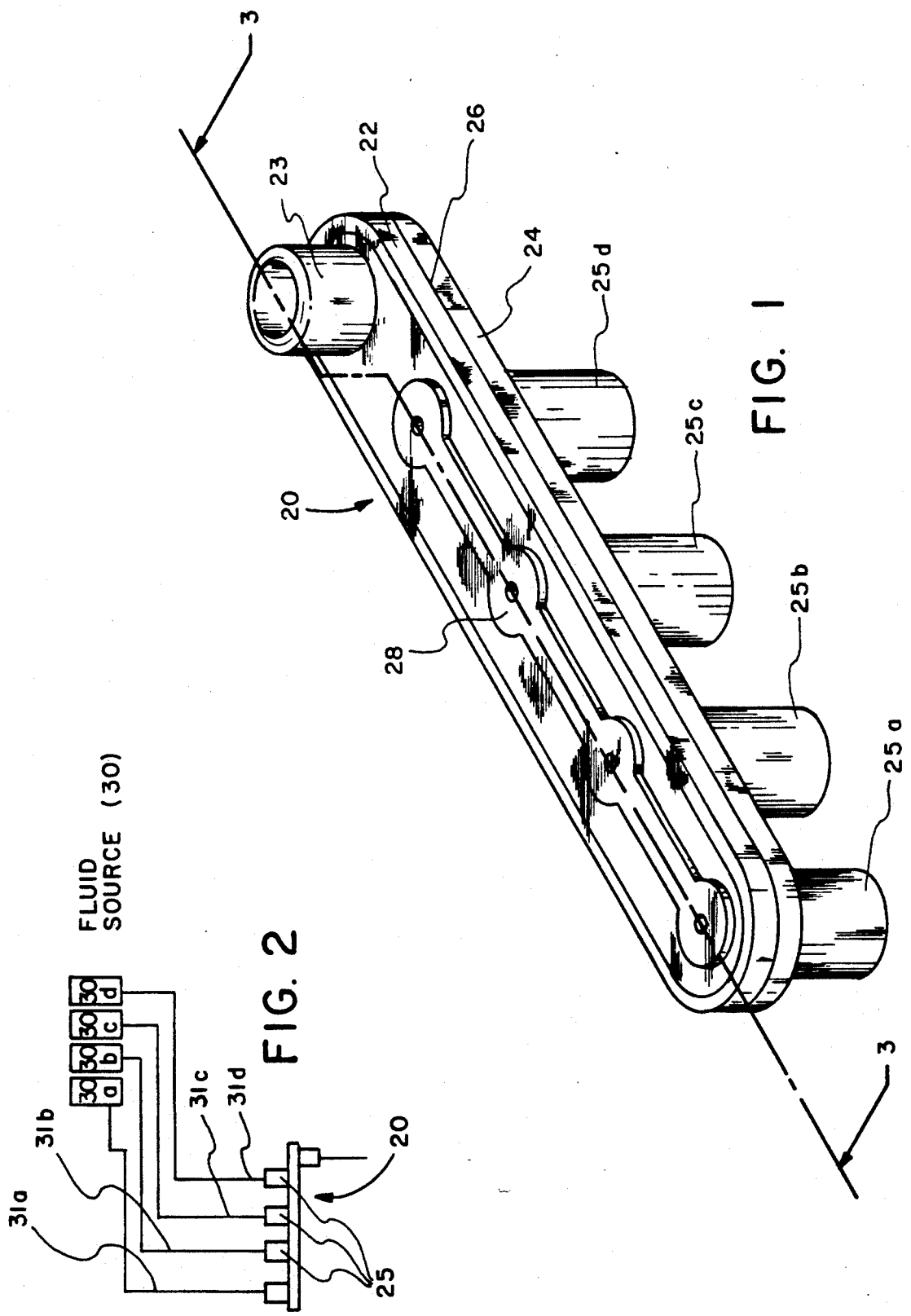

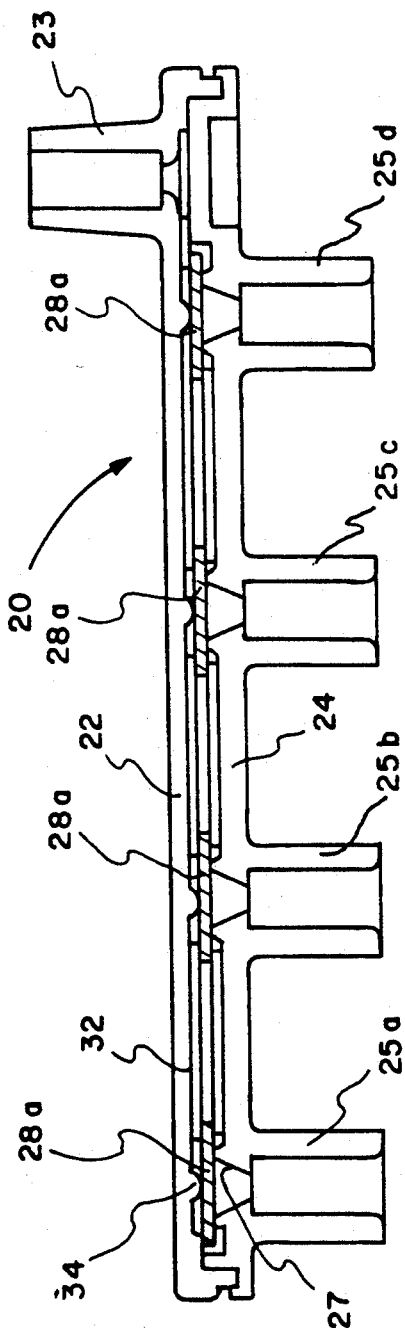
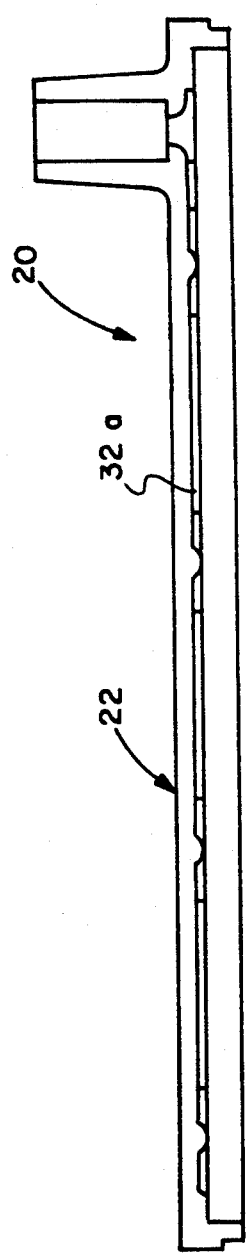
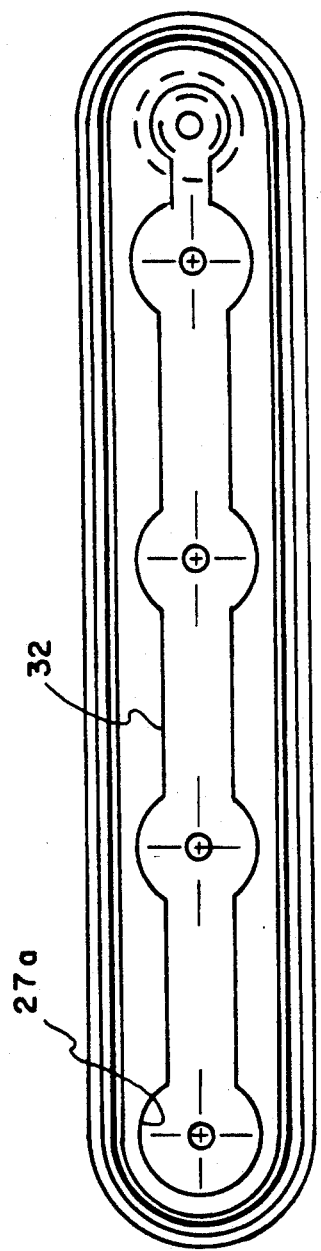

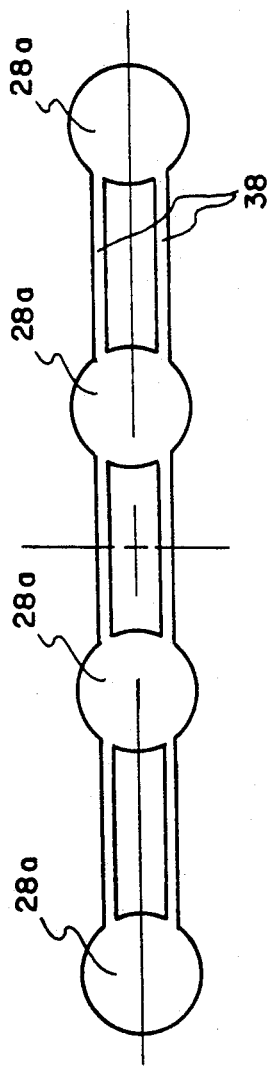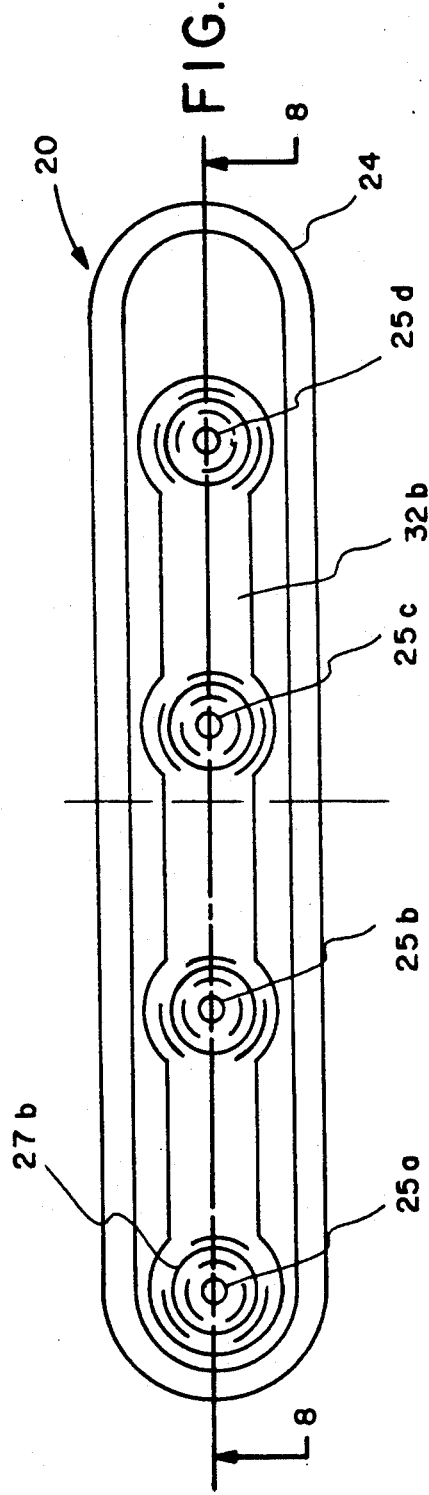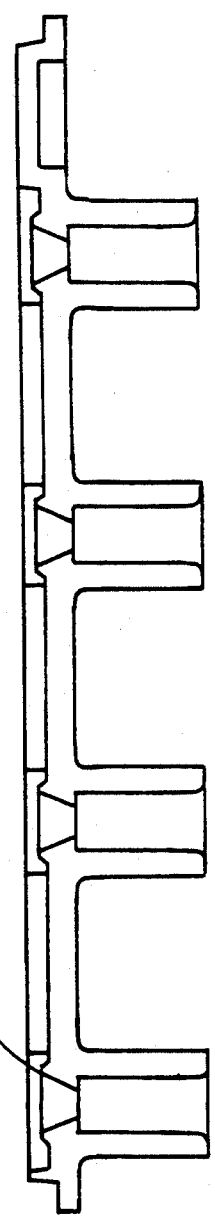

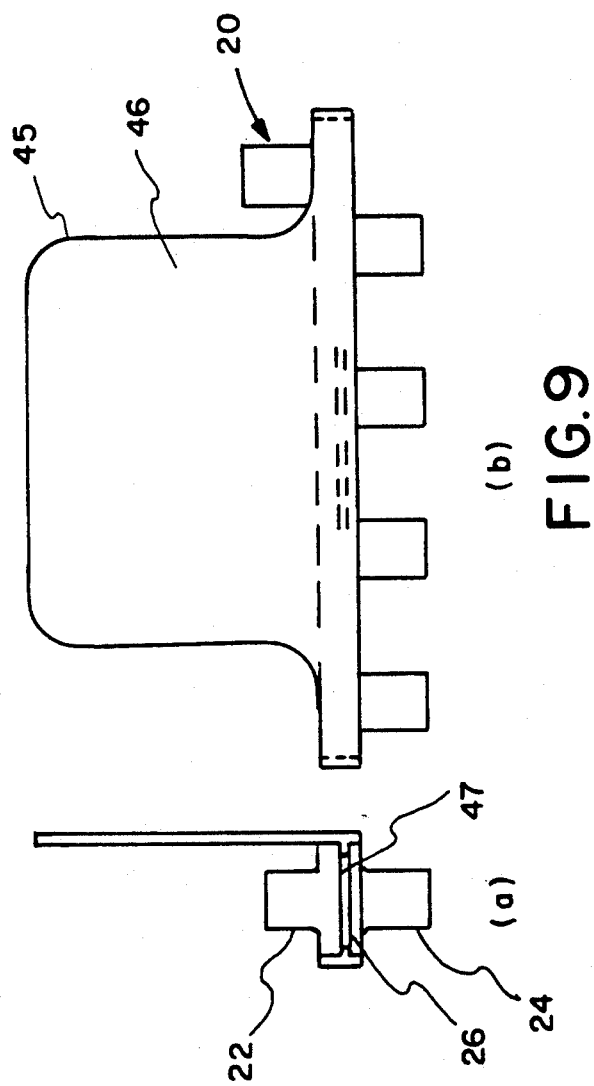

MULTI-VALVE MANIFOLD FOR DRUG INFUSION SYSTEMS

BACKGROUND OF THE INVENTION

1. Field of the Invention

This invention relates to an apparatus for controlling the infusion of fluids under pressure, including medical solutions and drugs. In particular, the present invention relates to a multi-valve infusion manifold having a plurality of inlet lines, a mixing chamber, and at least one outlet line; the manifold is used to administer a combination of fluids and drugs, such as anesthetics or cardiovascular medications, to a patient.

2. Description of the Prior Art

When it is necessary to administer a combination of drugs to a patient during a controlled medical procedure, such as anesthetizing a patient prior to and during surgery, or maintaining a patient on a combination of drugs during his stay in a cardiovascular care or intensive care unit, the known devices have substantial disadvantages.

For example, it is known to administer a combination of selected drugs by individual syringes, with each syringe connected to a stopcock which in turn is connected with a single primary IV set. In one known device, each stopcock has a control level which must be selectively and sequentially manually rotated to administer the desired combination of drugs to the patient. The level of accuracy associated with infusion rates and drug proportions associated with the aforementioned procedure is highly dependent on the skill of the attending medical professional. Potent anesthetic drugs must be precisely and accurately delivered, to avoid adverse effects on the patient. Other similar devices may use a manual stopcock in combination with a back check valve instead of a control lever.

Another manifold apparatus discloses a cannula assembly that includes a housing defining a fluid flow passage having two fluid inlets and one fluid outlet. One of the fluid inlets is shaped to receive the tip of an injection syringe for introduction of fluid to the inlet. Fluid flow through the inlet is controlled by a check valve housing an elastic tubular valve member closing off outlet openings associated with the check valve. Under sufficient pressure of a fluid in the inlet, the tubular valve member deflects outwardly permitting flow through the outlet openings.

A significant problem associated with such devices is back flow, which permits a solution in a delivery line to enter an adjacent delivery line, to produce an undesirable and unintended admixing of fluids within the input lines.

Further, each apparatus described above employs a multiplicity of parts. A multiplicity of parts makes each of the devices described above prone to unintentional leakages due to many fitment connections. In a multi-valve manifold, each valve may have a pre-set "cracking" pressure, which is normally the same for each inlet valve of the manifold. Cracking pressure is defined as the minimum pressure which opens the inlet valve.

Accordingly, it is desirable to provide an improved multi valve manifold which minimizes backflow, i.e., retrograde infusion or crosstalk from one inlet to another at the inlet valve locations. Further, it is desirable to provide a multi-valve manifold having substantially fewer parts than known devices, thus to minimize inadvertent leakage occurring at connections. Moreover, it is desirable to provide, within the constraints of a simplified manifold structure, means enabling variable preset pressure settings at each valve inlet. Such improvements would increase the effectiveness of the manifold, reduce its cost, and minimize the disadvantages and inefficiencies present in known devices.

SUMMARY OF THE INVENTION

In accordance with the present invention, a multi-valve manifold comprises two molded interconnecting members and a single flexible diaphragm interposed therebetween, representing a substantial reduction in parts as compared to known devices.

The multi-valve manifold of the present invention provides a first molded member carrying a multiplicity of valve inlets and a second interconnecting molded member having a single outlet. When the two manifold members are assembled, a mixing chamber is defined therebetween. Interposed within the mixing chamber is a flexible diaphragm which includes separate body portions aligned to overlie each of the valve inlets. Each valve inlet provides a respective internal member to engage a respective body portion of the diaphragm to close the valve inlets from the mixing chamber at a preset level of fluid pressure on the diaphragm (i.e., normally closed). Such internal member can be positioned to engage its respective diaphragm body portion at a preselected design height thus to define a preset cracking pressure for each valve inlet of the manifold.

An influx of fluid through a valve inlet will push against a respective body portion of the diaphragm to permit fluid to flow into the mixing chamber of the manifold once the cracking pressure for the valve inlet has been exceeded and thereafter through the outlet. When such fluid pressure decreases to a level below the cracking pressure, the valve inlet closes.

As thus described, the improved multi-valve manifold of the present invention provides a structure greatly simplified as compared to the known devices, substantially less costly as compared to such devices, and substantially more efficient than the known devices so as to minimize inadvertent fluid mixing at the valve inlets by easily establishing a preset cracking pressure for the inlets of the manifold and to readily enable the fluid passing through the manifold to follow the preferred path of fluid transfer from the inlet to the outlet. The advantages set forth above and other advantages shall become more apparent when the detailed description set forth below is considered in conjunction with the drawings provided herewith.

BRIEF DESCRIPTION OF THE DRAWINGS

The accompanying drawings illustrate one or more complete embodiments of the present invention according to the best mode so far devised for the practical applications of the principles thereof.

FIG. 1 is a top right perspective view of a multi-valve manifold constructed in accordance with the present invention;

FIG. 2 is a schematic representation of a typical application for the multi-valve manifold of the present invention;

FIG. 3 is a section through the multi-valve manifold of FIG. 1, taken along the line 3—3 thereof;

FIG. 4 is a side elevation of an upper member of the multi-valve manifold shown in FIG. 3;

FIG. 5 is a bottom plan view of the upper member of the multi-valve manifold shown in FIG. 4;

FIG. 6 is a top plan view of the diaphragm of the multi-valve manifold of FIG. 1;

FIG. 7 is a top plan view of the lower member of the multi-valve manifold of FIG. 1;

FIG. 8 is a sectional view taken along the lines 8—8 of FIG. 7; and

FIGS. 9a and 9b show the multi-valve manifold of FIG. 1 with an optional universal mounting bracket associated therewith secured in place.

DETAILED DESCRIPTION

As shown in FIG. 1, a multi-valve manifold 20 of the present invention includes a first molded member 22 having a fluid outlet port 23 provided therein, a second molded interconnecting member 24 having a multiplicity of fluid inlet ports 25 molded therein, with the members 22 and 24 adjoined or interconnected as by ultrasonic welding at a parting line 26 shown in FIG. 1. Retained at the interior of the multi-valve manifold 20 is a flexible diaphragm 28. The relationship of the interconnected members 22,24 will be described in greater detail below.

A typical application for the multi-valve manifold 20 of the present invention is an infusion pump or pumps having multiple channels In the application of FIG. 2, four separate infusion pump mechanisms 30a, 30b, 30c and 30d deliver pressurized fluids containing drugs through four fluid lines 31a, 31b, 31c and 31d connected to respective valve inlets 25a, 25b, 25c and 25d. The configuration shown in FIG. 2 is merely illustrative and other combinations of fluid delivery channels can be provided. Moreover, the multi-valve manifold 20 of the present invention is not limited to the specific configuration shown but may have more than 4 inlets, less than 4 inlets and more than one outlet.

The multi-valve manifold 20 of the present invention is shown in greater detail in FIGS. 3 through 8. FIG. 3, a sectional view taken along the lines 3—3 of FIG. 1, shows certain features of the manifold 20 in greater detail. For example, mixing channel 32 is shown between interconnected molded members 22 and 24 of the manifold 20. Further, inlet openings 25a,b,c,d of the inlets 25 are shown opening into the mixing channel 32. At the terminus of each of the inlet openings 25a is provided a valve seat 27 which receives a respective diaphragm closure member 28a seen section view in FIG. 3 and in plan view in FIG. 6. Each closure member 28a is cooperatively engaged by an interior protrusion 34 of the molded member 22 to hold the inlet 25 normally closed until the fluid in the connecting line 31 (FIG. 2) reaches a preset cracking pressure in the inlet.

Each protrusion 34 can also be modified to hold the valve inlet 25 closed at selected pressure levels. As best seen in FIG. 3, each protrusion 34 engages a respective diaphragm body portion 28a to retain each valve seat 27 closed against pressure exerted by fluid in the line 31 and the valve inlet 25. The length of protrusion 34 determines the force exerted against each diaphragm body portion 28a and thus sets the cracking pressure for each valve inlet 25a,b,c,d.

In the preferred embodiment, the length of each protrusion 34 is the same and the cracking pressure is designed to occur at a pre-selected level of either 1, 2, 3, 4 or 5 psi. However, the present structure is not limited to the cracking pressures chosen for the preferred embodiment, and far greater cracking pressures are possible, limited only by constraints imposed by the materials chosen and the practicality of the cracking pressures chosen. Moreover, it is not necessary to design a manifold member with all protrusions 34 of a single height, but rather the height of each protrusion 34 can be varied at each valve inlet 25 so as to vary the cracking pressure of that inlet, thereby enabling each inlet to operate at a different cracking pressure.

Similar considerations apply in the design of the diaphragm 28 and the valve seats 27. The thickness of the diaphragm body portions 28a can be changed to uniformly vary the cracking pressure to be defined by the manifold design, or the diaphragm 28 can be molded as a series of connected body portions 28a, each having a thickness selected to define the cracking pressure at the valve inlet 25 receiving the respective diaphragm body portion 28a. The depth of each valve seat 27a receiving a respective diaphragm body portion 28a can be similarly varied to enable a wide range of cracking pressures at each valve inlet site.

In the assembled state the inlet side of the multi-valve manifold 20 is sealed from its outlet side by the membrane 28, at a selected cracking pressure level and fluid at the inlets 25 must reach a predetermined pressure before the valve opens and fluid flows to the outlet.

FIGS. 4 and 5 show the molded member 22 of the outlet side of the multi-valve manifold 20, and in particular show the outlet portion 32a of the fluid mixing channel 32 of the manifold 20. The shape of the fluid channel 32 is better shown in FIG. 5 which also shows seats 27a for retaining the closure members 28a of the diaphragm 28 in place. Flexible membrane 28 is better shown in FIG. 6 which shows a series of valve closure members 28a joined by elongated connecting members 38 connected top and bottom between adjoining valve closure members. The connecting members 38 lie in the fluid mixing channel 30. With the valve closure member 28a in place, fluid is admitted to the mixing channel 32 only when the fluid pressure in an inlet opening 25 is sufficient to open the closure member 28a, and admit fluid to the mixing chamber 32. Thus, the construction of the preferred embodiment of the present invention prevents fluid mixing at the valve inlets 25, and substantially limits fluid mixing to the mixing chamber 32 of the multi-valve manifold 20.

In FIGS. 7 and 8 are shown more detailed views of the molded member 24 of the inlet side of the manifold 20. The molded member 24 includes the inlet side 32b of the mixing channel 32, including corresponding seats 27b, for the diaphragm members 28a, as well as valve openings 25a,b,c,d of the inlets 25.

FIGS. 9a and 9b display the multi-valve manifold 20 of the present invention with a mounting bracket 45 in place. Bracket 45 includes an upright leg 46 and a peripheral lip 47 which extends around the bracket 45 and snaps in place generally along the parting line 26 between the interconnecting first and second members 22,24 of the multi-valve manifold 20. The bracket 45 can be mounted on either side of the multi-valve manifold 20. Further, the bracket 45 is not limited to the configuration shown, but may be modified to conform to differing uses of the manifold 20.

It should be understood that the spacing of the inlet openings are a matter of design and are not a limiting feature of the present invention. Moreover, the position of the outlet manifold is also a matter of choice and such manifold need only be positioned such that its outlet opening has access to the mixing chamber 32 of the multi-valve manifold 20 of the present invention. In a consideration of the detailed description other changes and modifications of the preferred embodiment may be possible. However, such contemplated changes are intended to be embraced within the scope of the claims.

What is claimed is:

1. A multi-channel drug infusion system having a plurality of pumping mechanisms, each pumping mechanism having a separate fluid line for delivering fluid under pressure to a respective valve inlet of a multiple inlet manifold for mixing and transporting therethrough fluids under pressure, said manifold comprising:
   a manifold body comprising a first member including a plurality of valve inlets, each valve inlet including a respective valve seat, and a second member having at least one outlet said first and second members joined at a manifold body interface;
   a mixing chamber provided between the first and second members at the manifold body interface;
   and a flexible membrane disposed in the mixing chamber between the first and second members, the flexible membrane comprising separate valve seat portions, each valve seat portion aligned with and overlying a separate valve seat on the first member and held in place by a respective valve interior portion provided on the second member and opposite said valve seat portion to retain each of the valve inlets of the first member normally closed at a respective preset level of inlet pressure, with fluid under pressure exceeding said preset level pressing against a respective valve seat portion to open a respective valve inlet to enable fluid flow into the mixing chamber, each such valve seat portion opening and closing its respective valve inlet independently of the remaining valve inlets to minimize inadvertent mixing of fluids in the chamber or back flow to the inlets.

2. A multiple inlet manifold for mixing and transporting therethrough fluids under pressure, said manifold comprising:
   a manifold body comprising a first member including a plurality of valve inlets, each valve inlet including a respective valve seat, and a second member having at least one outlet, said first and second members joined at a manifold body interface;
   a mixing chamber provided between the first and second members at the manifold body interface;
   and a flexible membrane disposed in the mixing chamber between the first and second members, the flexible membrane comprising separate valve seat portions, each valve seat portion aligned with and overlying a separate valve seat on the first member and held in place by a respective valve interior portion provided on the second member and opposite said valve seat portion to retain each of the valve inlets of the first member normally closed at a respective preset level of inlet pressure, with fluid under a pressure exceeding said preset level pressing against a respective valve seat portion to open a respective valve inlet to enable fluid flow into the mixing chamber, each such valve seat portion opening and closing its respective valve inlet independently of the remaining valve inlets to minimize inadvertent mixing of fluids in the chamber or back flow to the inlets.

3. A multiple inlet manifold as claimed in claim 2 wherein said preset level is the same at each valve inlet.

4. A multiple inlet manifold as claimed in claim 1 wherein said preset level varies at each valve inlet.

5. A multiple inlet manifold as claimed in claim 4 wherein each interior portion of the valve provided on the second member comprises a protrusion which engages a respective membrane valve seat portion, the height of each protrusion to define a selected level of cracking pressure at each inlet, thus to independently preset the cracking pressure at each valve inlet.

6. A multiple inlet manifold as claimed in claim 4 wherein each valve seat portion is configured at varying selected thicknesses, the thickness of each body portion being selected to define a selected level of cracking pressure, thus to independently preset the cracking pressure at each valve inlet.

7. A multiple inlet manifold as claimed in claim 4 wherein each valve seat associated with a respective valve inlet has a preselected depth which defines a uniform valve inlet pressure, and the depth of each valve seat is varied to define a selected level of cracking pressure, thus to independently preset the cracking pressure at each valve inlet.

8. A multiple inlet manifold as claimed in claim 1 comprising four inlet valves and a single outlet.

9. A multiple inlet manifold as claimed in claim 1 including a bracket having a first portion including a peripheral lip engaging the manifold and a second portion, connected thereto including an upright member.

10. A multiple inlet manifold for mixing and transporting therethrough fluids under pressure, said manifold comprising:
   a manifold body comprising a first member including a plurality of valve inlets, each valve inlet including a respective valve seat, and a second member having one outlet, said first and second members joined at a manifold body interface;
   a mixing chamber provided between the first and second members at the manifold body interface;
   and a flexible membrane disposed in the mixing chamber between the first and second members, the flexible membrane comprising separate valve seat portions, each valve seat portion aligned with and overlying a separate valve seat on the first member and held in place by a respective valve interior portion provided on the second member and opposite said valve seat portion to retain each of the valve inlets of the first member normally closed at a respective preset level of fluid pressure, with fluid under a pressure exceeding said preset level pressing against a respective valve seat portion to open a respective valve inlet to enable fluid flow into the mixing chamber, each such valve seat portion opening and closing its respective valve inlet independently of the remaining valve inlets to minimize inadvertent mixing of fluids in the chamber or back flow to the inlets.

11. A multiple inlet manifold as claimed in claim 10 wherein said preset level is the same at each valve inlet.

12. A multiple inlet manifold as claimed in claim 10 wherein said preset level varies at each valve inlet.

13. A method for mixing and transporting fluids under pressure through a multiple inlet manifold, said method comprising the steps of:
   providing a manifold body comprising a first member including a plurality of valve inlets, each valve inlet including a respective valve seat, and a second member having a single outlet, with said first and second members joined at a manifold body interface;

providing a mixing chamber between the first and second members at the manifold body interface;

and disposing a flexible membrane in the mixing chamber between the first and second members, providing the flexible membrane with separate valve seat portions, aligning each valve seat portion to overlie a respective valve seat on the first member and holding each said valve seat portion in place by a respective valve interior portion provided on the second member and opposite said valve seat portion retain each of the valve inlets of the first member normally closed at a respective preset level of inlet pressure, pressing against a respective valve seat portion to open a respective valve inlet with fluid pressure exceeding said preset level to enable fluid flow into the mixing chamber, each such valve seat portion opening and closing its respective valve inlet independently of the remaining valve inlets to minimize inadvertent mixing of fluids in the chamber or back flow to the inlets.

14. The method claimed in claim 13 including the step of maintaining said preset level the same at each valve inlet.

15. The method as claimed in claim 13 including the step of varying said preset level at each valve inlet.

* * * * *